United States Patent [19]

Sano et al.

[11]  4,388,405

[45]  Jun. 14, 1983

[54] METHOD FOR PRODUCING L-HISTIDINE BY FERMENTATION

[75] Inventors: Kounosuke Sano, Tokyo; Takayasu Tsuchida, Kawasaki, both of Japan

[73] Assignee: Ajinomoto Company Incorporated, Tokyo, Japan

[21] Appl. No.: 158,876

[22] Filed: Jun. 12, 1980

[30] Foreign Application Priority Data

Jun. 25, 1979 [JP] Japan .................................. 54-79851

[51] Int. Cl.³ ...................... C12N 1/20; C12N 15/00; C12P 13/24; C12R 1/185
[52] U.S. Cl. .................................. 435/107; 435/253; 435/172; 435/848; 435/849
[58] Field of Search ............... 435/107, 172, 317, 848, 435/849, 253

[56] References Cited

U.S. PATENT DOCUMENTS

| 3,713,977 | 1/1973 | Nakayama et al. | 435/107 |
| 3,716,453 | 2/1973 | Okumura et al. | 435/107 |
| 4,237,224 | 12/1980 | Cohen et al. | 435/849 X |
| 4,278,765 | 7/1981 | Debabor et al. | 435/172 |

OTHER PUBLICATIONS

Moyed et al., Science, 129, 968–969, (1959).

Primary Examiner—Esther M. Kepplinger
Attorney, Agent, or Firm—Oblon, Fisher, Spivak, McClelland & Maier

[57] ABSTRACT

A microorganism of the genus Escherichia incorporated with a hybrid plasmid, which have been inserted with a DNA fragment possessing genetic information related to L-histidine production and obtained from a mutant of the genus Escherichia, resistant to a histidine-analogue, produces L-histidine in a high yield.

10 Claims, No Drawings

METHOD FOR PRODUCING L-HISTIDINE BY FERMENTATION

BACKGROUND OF THE INVENTION

This invention relates to a method for producing L-histidine by fermentation.

As to the fermentative production of L-histidine, auxotrophic or drug-resistant mutants of the genera, for example, Brevibacterium, Corynebacterium (U.S. Pat. No. 3,716,453) Escherichia (H. S. Moyed, M. Friedman: Science 129,968(1959)) and Serratia (Japanese Published Unexamined patent application No. 116296/1973) are known to produce.

SUMMARY OF THE INVENTION

The inventors chose a mutant of the genus Escherichia resistant to histidine-analogue as the deoxyribonucleic acid (hereinafter referred to as DNA) donor, then obtained from the mutant a DNA fragment possessing genetic information related to L-histidine production, and finally inserted the DNA fragment into a vector obtained from *Escherichia coli*. The recombinant plasmid was successfully introduced into a microorganism of Escherichia. It was found that the microorganism of this invention produces L-histidine in a yield much higher than hitherto known L-histidine producing mutants of the genus Escherichia.

DESCRIPTION OF THE PREFERRED EMBODIMENTS

The mutant of the genus Escherichia resistant to histidine analogue is known (H. S. Moyed, F. Friedman: Science 129,968 (1959)) and is obtained by usual artificial mutation techniques.

The histidine-analogue used in this invention inhibits the growth of the microorganism of the genus Escherichia, but the inhibition is suppressed by the presence of L-histidine partly or completely. Examples of histidine-analogue are 2-thiazolealanine, 1,2,4-triazole-alanine, 2-methyl-histidine and histidine-hydroxamate.

The DNA-donor employed in this invention also includes a mutant which has resistance to sulfa-drug such as sulfaguanidine, resistance to purine-analogue such as 8-azaguanine or requirement of amino acid such as tryptophan and methionine for growth together with the resistance to histidine-analogue. Usually, when DNA-donor which has higher productivety of L-histidine, more desirable results will be obtained.

Chromosomal DNA is extracted from the mutant by usual manner and treated with a restriction endonuclease by usual method.

The plasmid or phage DNA used as the vector is also treated with a restriction endonuclease by the analogous manner to the chromosomal DNA. Various kinds of restriction endonuclease can be used, if the digestion of the chromosomal DNA is done partially.

Thereafter, the digested chromosomal DNA and vector DNA are subjected to a ligation reaction.

Recombination of DNA can be carried out also by incorporating with terminaltransferase deoxyadenylic acid and thymidylic acid, or deoxyguanylic acid and deoxycytidylic acid to the chromosomal DNA fragment and cleaved vector DNA, and by subjecting the modified chromosomal DNA fragment and cleaved DNA to annealing.

As the vector DNA, conventional vector derived from plasmid or phage can be employed such as Col EI, pSC 101, pBR 322, and R6K.

The hybrid DNA thus obtained can be incorporated into a microorganism of the genus Escherichia by conventional transformation technique. The desired transformant is screened using a medium on which a clone, having one or both of the characteristics of L-histidine productivity possessed by chromosomal DNA fragment and those possessed by vector DNA, can only grow.

As the recipient of the hybrid DNA, any strains of the genus Escherichia can be used.

In order to increase the productivity, the recipient is desirably given nutritional requirement of, for instance, L-isoleucine, L-proline, L-arginine, L-methionine, L-tryptophane, L-leucine, L-tyrosine, L-lysine, guanine and xanthine, and resistance to, for instance, sulfamethomidine, ethionine, 2-aminobenzothiazole, 8-azaguanine, 8-azaadenine, 2,6-diaminopurine, methionine-sulfoxide, 4-aminopyrazole-3,4-dipyridine, 1,2,4-triazolealanine, in single or in combination. Desirably, mutant having higher productivity of L-histidine is used as the recipient.

It is preferable that the resistance or nutritional requirement as above is possessed also by the DNA donor.

The method of culturing the L-histidine producing strain thus obtained are conventional, and are similar to the methods for the cultivation of known L-histidine producing microorganisms. Thus, the culture medium is a conventional one containing carbon sources, nitrogen sources, inorganic ions and, when required, minor organic nutrients such as vitamines or amino acids. Examples of the carbon sources are, glucose, fructose sucrose and lactose, and crude materials containing the carbon source such as starch hydrolysate and molasses. Gaseous ammonia, aqueous ammonia and ammonium salts and other conventional nitrogen source can be used as the nitrogen source. More desirable result will be obtained when more than 50 mg/dl purine compound such as adenine, adenosine, adenylic acid, hypoxanthine, inosine, inosinic acid is added to the medium.

Cultivation is carried out under aerobic condition adjusting the pH and the temperature of the medium at a suitable level and continued until the formation of L-histidine ceases substantially. L-Histidine accumulated in the culture medium can be recovered by conventional manners.

According to the present invention, L-histidine can be produced in a higher yield than the known methods using Escherichia strains. Moreover, the amount of by-produced amino acids is scarce and, accordingly, L-histidine can be recovered through a simple process in a high yield.

EXAMPLE 1

(1) Preparation of chromosomal DNA possessing genetic information related to L-histidine production.

*Escherichia coli* R-344 (NRRL B-12220), a mutant resistant to 2-thiazole-alanine (2TA) and induced from K-12(ATCC 10798), was cultured at 37° C. for 3 hours with shaking in 1 l of L-medium containing 1g/dl peptone, 0.5 g/dl yeast extract, 0.1 g/dl glucose and 0.5 g/dl NaCl (pH was adjusted to 7.2), and bacterial cells in exponential growth phase were harvested. Chromosomal DNA was extracted by conventional phenol-method, and 5.3 mg of purified DNA were obtained.

(2) Preparation of vector DNA.

As the vector, DNA of plasmid pBR 322, which contains both ampicillin and tetracycline resistance genes as makers, was prepared as follows:

A strain of *Escherichia coli* K-12 harboring the plasmid pBR 322 was incubated at 37° C. in 1 l of a glucose-"casamino acid"-inorganic salts medium, containing, 2 g glucose, 1 g $HN_4Cl$, 6 g $Na_2HPO_4$, 3 g $KH_2PO_4$, 5 g NaCl, 0.1 g $MgSO_4.7H_2O$, 0.015 g $CaCl_2.2H_2O$, 20 g "casamino acid" (casein-hydrolysate), 0.05 g L-tryptophan, 0.05 g thymine and 100 μg thiamine.HCl, per liter (pH was adjusted to 7.2). After an incubation had been carried out until late log phase, 170 μg/ml of chloramphenicol was added to the culture medium. Through this process, the plasmid DNA was amplified and accumulated abundantly in the bacterial cells.

After 16 hours of the incubation, cells were harvested and then lysed by treatment with lysozyme and SDS. The lysate was centrifuged at 30,000×g for 1 hour to obtain supernatant. After concentrating the supernatant, 580 μg of the plasmid DNA was obtained by fractionation using cesium chloride-ethidium bromide equilibrium density gradient centrifugation.

(3) Insertion of chromosomal DNA fragment into vector.

Ten μg of the chromosomal DNA was treated with each of the restriction endonuclease EcoRI, Pst I and Hind III at 37° C. for 5, 10, 20, 30 and 60 minutes respectively, to cleave DNA chains, and then heated at 65° C. for 5 minutes, respectively. Ten μg of the vector DNA was also treated with each of the restriction enconucleases, EcoRI, Pst I and Hind III at 37° C. for 1 hour to cleave the DNA completely, and then heated at 65° C. for 5 minutes, respectively.

The digested chromosomal DNA solution and cleaved vector DNA solution were mixed and subjected to the ligation reaction of DNA fragments by the $T_4$ phage DNA-ligase in the presence of ATP and dithiothreitol at 10° C. for 24 hours. The reaction mixture was then heated at 65° C. for 5 minutes, and two folds volume of ethanol was added to it. Thus precipitated recombinant DNA was recovered.

(4) Genetic transformation with the hybrid plasmid harboring the genetic information related to L-histidine production.

An L-histidine-requiring strain of *Escherichia coli* H-13 (NRRL B-12219), which was derived from *Escherichia coli* K-12 by N-methyl-N'-nitro-N-nitrosoguanidine mutagenesis, was cultured in 10 ml of L-medium at 37° C. with shaking. Cells in exponential growth phase were harvested, and suspended in 0.1 M $MgCl_2$ solution and then in 0.1 M $CaCl_2$ solution in an ice-bath, whereby, "competent" cells having the ability of DNA uptake were prepared.

Into the competent cells suspension, the DNA obtained in step (3), which contains the hybrid plasmid DNA, was added. The suspension was kept in an ice-bath for 30 minutes, then heated at 42° C. for 2 minutes, and again allowed to stand in an ice-bath for 30 minutes, the cells, thus being incorporated with the hybrid plasmid DNA, were inoculated into L-medium and the medium was shaken at 37° C. for 3 hours, whereby the transformation reaction was completed. The cells were harvested, washed, and resuspended. A small portion of the cells suspension was spread on an agar plate containing, 2 g glucose, 1 g $(NH_4)_2SO_4$, 7 g $K_2HPO_4$, 2 g $KH_2PO_4$, 0.1 g $MgSO_4.7H_2O$, 0.5 g sodium citrate.2-$H_2O$ and 2 g agar, per liter, (pH was adjusted to 7.2).

The plate was incubated at 37° C. After 3 days incubation, all of the colonies appeared were picked up, purified and isolated.

Colonies, which are resistant to at least one antibiotic of ampicillin and tetracycline and have the ability of producing L-histidine were obtained as the transformant. Resistance to ampicillin (50 μg/ml) and to tetracycline (5 μg/ml) was tested using agar-L-medium, and L-histidine productivity was examined by the formation of halo on a minimum-agar-medium on which L-histidine requiring mutant H-13 had previously been spread.

Thus, AJ 11378 (FERM-P 5038, NRRL B-12116) containing the plasmid treated with Hind III, AJ 11385 (FERM-P 5045, NRRL B-12118) containing the plasmid treated with EcoRI, and AJ 11386 (FERM-P 5046, NRRL B-12119) containing the plasmid treated with Pst I were obtained.

(5) Production of L-histidine by the novel L-histidine-producing strain.

Table 1-A shows the experimental result of the fermentative production of L-histidine using the strains AJ 11378, AJ 11385 and AJ 11386, in comparison with the DNA donor R-344.

Table 1-B shows the experimental result of fermentative production of L-histidine using another novel L-histidine-producing strains obtained as follows:

The plasmid harboring the genetic information related to L-histidine production was extracted from AJ 11378. While, to the strain R-344, resistance to 1,2,4-triazolealanine was given, obtaining R-344-34 (NRRL B-12221).

AJ 11387 (FERM-P 5047, NRRL B-12120) and AJ 11388 (FERM-P 5048, NRRL B-12121) were obtained by incorporating the hybrid plasmid into R-344 and R-344-34, respectively.

The fermentation medium contained 5 g/dl glucose, 2.5 g/dl ammonium sulfate, 0.2 g $KH_2PO_4$, 0.1 g/dl $MgSO_4.7H_2O$, 0.05 g/dl yeast extract, 100 μg/dl thiamine.HCl, 1 mg/dl $FeSO_4.7H_2O$, 1 mg/dl $MnSO_4.4H_2O$ and 2.5 g/dl $CaCO_3$ (separately sterilized) and the pH was adjusted to 7.0.

Twenty ml batches of the fermentation medium was placed in 500 ml flasks, inoculated with one loopful inoculum of the test microorganism, and the cultivation was carried out at 31° C. for 72 hours.

The amount of L-histidine in the supernatant of the fermentation broth was determined by microbiological assay.

| Microorganism tested | | L-histidine produced (mg/dl) |
|---|---|---|
| A | R-344 | 6.0 |
| | AJ 11378 | 15 |
| | AJ 11385 | 25 |
| | AJ 11386 | 18 |
| B | AJ 11378 | 10 |
| | AJ 11387 | 42 |
| | AJ 11388 | 255 |

What is claimed as new and intended to be covered by Letters Patent is:

1. A method for producing L-histidine by fermentation which comprises: culturing in a culture medium an L-histidine producing microorganism selected from the group consisting of *Escherichi coli* NRRL B-12116, *Escherichia coli* NRRL B-12118, *Escherichia coli* NRRL B-12119, *Escherichia coli* NRRL B-12120 and *Escherichia coli* NRRL B-12121, which is produced by incorporating a hybrid plasmid into a recipient strain of the genus "Escherichia", said hybrid plasmid containing a deoxy-ribonucleic acid fragment possessing genetic information related to L-histadine production, obtained from a mutant of the genus "Escherichia", resistant to a histidine analogue; and recovering the L-histidine accumulated in the culture medium.

2. The method of claim 1, wherein said histidine-analogue is 2-thiazolealanine, 1,2,4-trialolealanine or histidine-hydroxamate.

3. The method of claim 1, wherein said recipient belongs to *Escherichia coli.*

4. The method of claim 1, wherein said mutant belongs to *Escherichia coli.*

5. A bacterium of the genus Escherichia which is *Escherichia coli* NRRL B-12116.

6. A bacterium of the genus Escherichia which is *Escherichia coli* NRRL B-12118.

7. A bacterium of the genus Escherichia which is *Escherichia coli* NRRL B-12119.

8. A bacterium of the genus Escherichia which is *Escherichia coli* NRRL B-12120.

9. A bacterium of the genus Escherichia which is *Escherichia coli* NRRL B-12121.

10. A method for producing L-histidine by fermentation which comprises:

culturing in a culture medium an L-histidine producing microorganism selected from the group consisting of *Escherichia coli* NRRL B-12116, *Escherichia coli* NRRL B-12118 or *Escherichia coli* NRRL B-12119 which is produced by incorporating a hybrid plasmid into a recipient strain of the genus "Escherichia", said hybrid plasmid containing a deoxyribonucleic acid fragment possessing genetic information related to L-histidine production, obtained from a mutant of the genus "Escherichia" resistant to a histidine-analogue, said recipient strain of the genus "Escherichia" being an L-histidine-requiring strain;

and recovering the L-histidine accumulated in the culture medium.

* * * * *